US008894796B2

(12) United States Patent
Hall et al.

(10) Patent No.: US 8,894,796 B2
(45) Date of Patent: Nov. 25, 2014

(54) NANOPORE FABRICATION AND APPLICATIONS THEREOF

(75) Inventors: Adam R Hall, Clemmons, NC (US); Jijin Yang, Acton, MA (US); David C Ferranti, Concord, MA (US); Colin A Sanford, Atkinson, NH (US)

(73) Assignees: The University of North Carolina at Greensboro, Greensboro, NC (US); Carl Zeiss NTS, LLC, Peabody, MA (US)

( * ) Notice: Subject to any disclaimer, the term of this patent is extended or adjusted under 35 U.S.C. 154(b) by 0 days.

(21) Appl. No.: 14/124,434

(22) PCT Filed: Jun. 6, 2012

(86) PCT No.: PCT/US2012/041058
§ 371 (c)(1),
(2), (4) Date: May 15, 2014

(87) PCT Pub. No.: WO2012/170499
PCT Pub. Date: Dec. 13, 2012

(65) Prior Publication Data
US 2014/0319339 A1    Oct. 30, 2014

Related U.S. Application Data

(60) Provisional application No. 61/493,811, filed on Jun. 6, 2011.

(51) Int. Cl.
| | |
|---|---|
| *G01N 23/00* | (2006.01) |
| *G01N 23/02* | (2006.01) |
| *H01J 37/30* | (2006.01) |
| *H01J 37/305* | (2006.01) |
| *H01J 37/26* | (2006.01) |
| *G01N 15/10* | (2006.01) |
| *G01N 15/00* | (2006.01) |

(52) U.S. Cl.
CPC ........... *H01J 37/3056* (2013.01); *H01J 37/261* (2013.01); *G01N 15/10* (2013.01); *G01N 2015/0065* (2013.01); *Y10S 977/924* (2013.01)

USPC ............... 156/252; 156/272.2; 250/492.2; 977/924

(58) Field of Classification Search
CPC ............... C12Q 2565/631; G01N 33/48721; B82Y 15/00; B01L 3/5027
USPC ............. 977/924; 250/492.2; 156/252, 272.2
See application file for complete search history.

(56) References Cited

U.S. PATENT DOCUMENTS

| | | | |
|---|---|---|---|
| 6,093,445 | A | 7/2000 | Nawate |
| 2002/0122873 | A1 | 9/2002 | Mirkin et al. |

(Continued)

OTHER PUBLICATIONS

Yang et al, Rapid and precise scanning helium ion microscope milling of solid-state nanopores for biomolecule detection; Nanotechnology, Jun. 10, 2011, 6 pgs, vol. 22, No. 28, 285310, IOP Publishing, Bristol, GB.

(Continued)

*Primary Examiner* — Nikita Wells
(74) *Attorney, Agent, or Firm* — Smith Moore Leatherwood LLP; Clint Wimbish (57) ABSTRACT

In one aspect, methods of nanopore formation in solid state membranes are described herein, In some embodiments, a method of forming an aperture comprises providing at least one solid state membrane in a chamber, selecting a first dose of ions sufficient to provide a first aperture of predetermined diameter through the membrane and exposing a surface of the membrane at a first location to the first dose of ions in a focused ion beam having a focal point of diameter less than or equal to about 1 nm to remove material from the membrane at the first location thereby providing the first aperture having the predetermined diameter or substantially the predetermined diameter.

20 Claims, 6 Drawing Sheets

(56) References Cited

U.S. PATENT DOCUMENTS

2007/0042366 A1* 2/2007 Ling .................................. 435/6
2011/0053284 A1* 3/2011 Meller et al. ................... 436/149
2013/0309776 A1* 11/2013 Drndic et al. .................... 436/94

OTHER PUBLICATIONS

International Search Report and Written Opinion for International Appl. No. PCT/US2012/041058 mailed on Jan. 21, 2013; 15 pgs.

* cited by examiner

NANOPORE FABRICATION AND APPLICATIONS THEREOF

RELATED APPLICATION DATA

The present application is the national stage application under 35 U.S.C. §371 of International Application No. PCT/US2012/041058, filed Jun. 6, 2012, which claims priority pursuant to 35 U.S.C. §119(e) to U.S. Provisional Patent Application Ser. No. 61/493,811, filed Jun. 6, 2011, which is hereby incorporated by reference in its entirety.

FIELD

The present invention relates to solid state structures and, in particular, to methods of forming nanometer scale pores in solid state membranes.

BACKGROUND

Solid-state nanopores are among a class of devices capable of biological analysis at the single-molecule level. To this point, a limited number of reliable nanopore formation methods have been reported. The two most widely used techniques are sculpting with a low energy ion beam and sputtering with a transmission electron microscope (TEM). In the former method, an ion sputtering system is used to controllably close a preformed opening of initial diameter of about 100 nm in a substrate. Using a feedback system capable of accurately detecting transmitted ion flux, single nanopores have been produced according to this technique with diameters as low as 1-2 nm. In the latter method, the tightly focused beam of a TEM is used to locally ablate a thin, free-standing solid-state membrane resulting in the formation of an individual nanopore. Subsequent exposure with a beam of reduced energy is then used to fluidize the membrane, slowly closing the initially formed pore with single nanometer precision.

The dimensional control and advantages offered by these fabrication techniques, however, is largely offset by slow membrane processing times leading to limited throughput. In both the low energy ion beam and TEM techniques, for example, only a single substrate or membrane can be processed at one time. Furthermore, nanopore backfill/shrinking processes can require several minutes to over an hour for completion. In view of these temporal processing disadvantages, large scale production of nanopore analytical devices remains unrealized.

SUMMARY

In one aspect, methods of nanopore formation in solid state membranes are described herein which, in some embodiments, can offer one or more advantages over current nanopore fabrication techniques. In some embodiments, for example, single step nanopore fabrication methods are described herein which may lead to the efficient manufacture of solid-state membranes for the detection and/or analysis of molecular species.

In some embodiments, a method described herein comprises providing at least one solid state membrane in a chamber, selecting a first dose of ions sufficient to provide a first aperture of predetermined diameter through the membrane and exposing a surface of the membrane at a first location to the first dose of ions in a focused ion beam having a focal point of diameter less than or equal to about 1 nm to remove material from the membrane at the first location thereby providing the first aperture having the predetermined diameter or substantially the predetermined diameter. In some embodiments, the first dose of ions sufficient to provide the first aperture is selected with reference to data derived from one or more reference membranes comprising one or more structures formed by exposure to quantified doses of ions in an ion beam.

In some embodiments, a method described herein further comprises selecting an additional dose of ions sufficient to provide an additional aperture of predetermined diameter through the membrane and exposing a surface of the membrane at an additional location to the additional dose of ions in an ion beam. Exposure of the membrane surface to the ion beam removes material from the membrane at the additional location to provide the additional aperture having the predetermined diameter or substantially the predetermined diameter.

In some embodiments, a plurality of additional ion doses is selected, and surfaces of the membrane are exposed to the additional ion doses in ion beams at additional locations, thereby removing material from the membrane to provide additional apertures having the predetermined diameter or substantially the predetermined diameter. The apertures, in some embodiments, are arranged in an array format such as a one-dimensional array or a two-dimensional array. Moreover, in some embodiments, one or more additional apertures in a solid state membrane are fabricated without removing the membrane from the chamber or otherwise further processing the membrane between ion beam exposures.

An additional dose of ions forming an additional aperture, in some embodiments, is determined by reference to data derived from a reference membrane comprising one or more structures formed by exposure to quantified doses of ions of an ion beam.

In some embodiments, a method described herein further comprises thinning the solid state membrane in an area proximate the first aperture. In some embodiments, thinning the membrane comprises exposing an area proximate the first aperture to an ion beam. The ion beam for thinning, in some embodiments, employs the same ionic species as the ion beam for formation of the first aperture. In some embodiments, the ion beam moves in a predetermined pattern to thin the membrane. Ion thinning of the membrane, in some embodiments, is conducted without masking and/or lithographic developing procedures.

Additionally, in some embodiments, a dose of ions sufficient to thin the membrane is determined by reference to data derived from one or more reference membranes comprising one or more structures formed by exposure to quantified dose(s) of ions of an ion beam. In some embodiments, thinning the membrane is administered prior to aperture formation. In some embodiments, thinning the membrane is administered subsequent to aperture formation.

In some embodiments, thinning of a solid state membrane is administered while the membrane is in the aperture formation chamber, thereby precluding additional processing requiring separation of the membrane from the chamber prior to aperture formation. In one embodiment, for example, a membrane is placed in the chamber and thinned with an ion beam in an area proximate to where an aperture is to be formed. After completion of the thinning, aperture formation can begin without the need to further process the membrane outside to the chamber prior to aperture formation. This is in sharp contrast to prior techniques where a membrane is thinned by electron beam lithography, chemical etch or combinations thereof prior to placement in a chamber for exposure to an ion source.

In some embodiments of methods described herein, a plurality of solid-state membranes is provided in the chamber, wherein the membranes are exposed to a first dose of ions providing first apertures of predetermined diameter through the membranes as described herein. Moreover, in some embodiments, the membranes are exposed to additional doses of ions at a plurality of additional locations providing additional apertures of predetermined diameter as described herein. The ability to process a plurality of membranes during an aperture formation step in a single chamber marks a fundamental departure from prior nanopore fabrication techniques limited to processing only one solid state membrane at a time per aperture formation chamber.

In some embodiments, a method described herein further comprises exposing the first aperture and/or additional aperture to an unfocused ion beam. Exposure of the first aperture and/or additional aperture to an unfocused ion beam, in some embodiments, reduces the diameter of the aperture. In some embodiments, the diameter of the aperture is reduced by material transported to the aperture in response to exposure by the defocused ion beam.

In another aspect, a method described herein comprises providing at least one solid state membrane in a chamber, exposing a surface of the membrane at a first location to a first dose of ions in a focused ion beam sufficient to provide a first aperture of first diameter through the membrane, wherein the first dose of ions falls in a first linear region of a plot of aperture diameter versus ion dose having a slope [(aperture diameter)/(ion dose)] greater than a second linear region of the plot. In some embodiments, the method further comprises exposing a surface of the membrane at a second location to a second dose of ions in a focused ion beam sufficient to provide a second aperture of second diameter through the membrane, wherein the second dose of ions falls in the first linear region or the second linear region of the plot of aperture diameter versus ion dose. In some embodiments, the membrane is exposed to the second dose of ions prior to exposure to the first dose of ions. In some embodiments, the membrane is thinned in an area proximate the first aperture and/or second aperture. In some embodiments, the membrane is thinned while in the aperture formation chamber as described further herein.

In another aspect, a method described herein comprises providing at least one solid state membrane in an aperture formation chamber, selecting a first dose of ions sufficient to provide a first aperture through the membrane and exposing a surface of the membrane at a first location to the first dose of ions in an ion beam to provide the first aperture, wherein the membrane is thinned in the formation chamber in an area proximate the first aperture. In some embodiments, the membrane is thinned in a step prior or subsequent to formation of the first aperture. In some embodiments, the method further comprises selecting an additional dose of ions sufficient to provide an additional aperture through the membrane and exposing a surface of the membrane at an additional location to the additional dose of ions in an ion beam to provide the additional aperture. In some embodiments, the membrane in also thinned in the chamber in an area proximate the additional aperture. In some embodiments, the membrane is thinned in a step prior or subsequent to formation of the additional aperture. Thinning the membrane, in some embodiments, comprises exposing the membrane to an ion beam. In some embodiments, the ion beam for thinning the membrane employs the same ionic species as the ion beam forming the first and/or additional apertures.

In another aspect, methods of conducting particle analysis are described herein. In some embodiments, a method of conducting particle analysis comprises providing a solid state membrane comprising an aperture and passing a particle through the aperture to determine or more properties of the particle, wherein the aperture is formed by any method described herein. In some embodiments, for example, the aperture is formed by exposing a surface of the membrane at a first location to a dose of ions in an ion beam having a focal point of diameter less than or equal to about 1 nm to remove material from the solid state membrane at the first location. In some embodiments, the membrane is thinned in an area proximate the aperture according to methods described herein.

Further, in some embodiments of methods of conducting particle analysis, the dose of ions is selected to provide the aperture a predetermined diameter as described herein. The dose of ions, in some embodiments, falls in a first linear region of a plot of aperture diameter versus ion dose, the first linear region having a slope greater than a second linear region of the plot. Alternatively, in some embodiments, the dose of ions falls in the second linear region of the plot.

In some embodiments, the solid state membrane is placed between electrically isolated ionic solutions and a voltage is applied to pass the particle through the aperture in the membrane.

These and other embodiments are described in greater detail in the detailed description which follows.

DETAILED DESCRIPTION

The present invention can be understood more readily by reference to the following detailed description and drawings and their previous and following descriptions. Elements, apparatus and methods of the present invention, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

I. Methods of Nanopore Formation

In one aspect, methods of nanopore formation in solid state membranes are described herein. In some embodiments, a method described herein comprises providing at least one solid-state membrane in a chamber, selecting a first dose of ions sufficient to provide a first aperture of predetermined diameter through the membrane and exposing a surface of the membrane at a first location to the first dose of ions through a focused ion beam having a focal point of diameter less than or equal to about 1 nm to remove material from the membrane at the first location thereby providing the first aperture having the predetermined diameter or substantially the predetermined diameter. In some embodiments, a focused ion beam of a method described herein is destigmated. In some embodiments, the first dose of ions sufficient to provide the first aperture of predetermined diameter is selected with reference to data derived from one or more reference membranes comprising one or more structures formed by exposure to quantified ion doses of an ion beam.

A first aperture of a solid state membrane fabricated according to any method described herein can have any desired diameter on the nanometer scale. In some embodiments, a first aperture has a diameter of less than about 10 nm. In some embodiments, a first aperture has a diameter of less than about 5 nm or less than about 4 nm. In some embodiments, a first aperture has a diameter of greater than about 10 nm. In some embodiments a first aperture has a diameter or at least about 15 nm or at least about 20 nm. In some embodiments, a first aperture has a diameter of at least about 25 nm. In some embodiments, a first aperture has a diameter ranging from about 2 nm to about 30 nm or from about 3 nm to about 20 nm. In some embodiments, a first aperture has a diameter ranging from about 5 nm to about 15 nm. In some embodiments, a first aperture has a diameter ranging from about 1 nm to about 9 nm or from about 2 nm to about 8 nm. In some embodiments, a first aperture has a diameter ranging from about 3 nm to about 8 nm. In some embodiments, a first aperture has a diameter ranging from about 1 nm to about 5 nm or from about 1.5 nm to about 4 nm. In some embodiments, a first aperture has a diameter suitable for detecting and/or conducting analysis of one or more single molecular species.

In some embodiments, a first aperture is fabricated according to methods described herein in a time period less than 60 seconds or less than 45 seconds. In some embodiments a first aperture is fabricated in a time period less than 30 seconds or less than 15 seconds. In some embodiments, a first aperture is fabricated in a time period less than 12 seconds or less than 10 seconds. In some embodiments, a first aperture is fabricated in a time period less than 5 seconds or less than 1 second. In some embodiments, a first aperture is fabricated on the order of milliseconds (ms).

In some embodiments, a first aperture is fabricated in a time period ranging from about 50 ms to about 15 seconds. In some embodiments, a first aperture is fabricated in a time period ranging from about 100 ms to about 5 seconds or from about 200 ms to about 1 second.

Turning now to components of methods, methods described herein comprise a solid state membrane. In some embodiments, a solid state membrane is non-metallic. A non-metallic solid-state membrane, in some embodiments, comprises one or more electrically insulating materials. In some embodiments, a solid-state membrane is a ceramic material. A ceramic can comprise a metal oxide, metal nitride, metal carbide or metal carbonitride or combinations thereof. In some embodiments, a ceramic suitable for use in some embodiments of methods described herein is silicon nitride (SiN, $Si_3N_4$). In some embodiments, a ceramic comprises silicon oxide, silicon carbide, aluminum oxide or a transition metal oxide. In some embodiments, a ceramic membrane is polycrystalline in nature. In some embodiments, a ceramic is single crystalline in nature. In some embodiments, a ceramic membrane is multilayered. Individual layers of a multilayered membrane can comprise the same material or divergent materials. In some embodiments, individual layers of a ceramic membrane are independently selected from the group consisting of a transition metal carbide, transition metal nitride, transition metal carbonitride, transition metal oxide, alumina, silica and SiN.

In some embodiments, a solid state membrane comprises one or more semiconducting materials. In some embodiments, a suitable semiconducting material comprises a II/VI semiconductor, Group IV semiconductor or a III/V semiconductor. In some embodiments, a semiconductor comprises a ternary semiconductor or a quaternary semiconductor. In some embodiments, a semiconductor has an amorphous structure. In some embodiments, a semiconductor has a crystalline structure, including a single crystalline structure or a polycrystalline structure.

In some embodiments, a solid state membrane is metallic. In such embodiments, a solid state membrane can be a metal or various alloys of metals. In some embodiments, for example, suitable metals are transition metals, including noble metals. Alternatively, a solid state membrane, in some embodiments, is not gold.

In some embodiments, a solid state membrane comprises an organic material. In some embodiments, for example, a solid state membrane comprises one or more polymeric materials. In some embodiments, suitable polymeric material comprise thermoplastics, thermosets or elastomers.

A solid state membrane suitable for methods described herein can have any desired thickness. In some embodiments, a solid state membrane has a thickness suitable for detecting and/or conducting analysis of one or more molecular species. In some embodiments, a solid state membrane has a thickness less than about 200 nm or less than about 100 nm. In some embodiments, a solid state membrane has a thickness less than about 50 nm. In some embodiments, a solid state membrane has a thickness ranging from about 5 nm to about 100 nm. In some embodiments, a solid state membrane has a thickness ranging from about 10 nm to about 80 or from about 20 to about 60 nm. In some embodiments, a solid-state membrane has a thickness ranging from about 30 nm to about 50 nm. In some embodiment, the thickness of a solid state membrane is measured prior to aperture formation according to a method described herein.

In some embodiments, ions suitable for use in methods described herein are selected according to the ability to form a focused ion beam having a desired focal point diameter. In some embodiments, suitable ions are selected according to the ability to resist implantation into the solid state membrane. In some embodiments, for example, ions of a first dose comprise ions of a noble gas. A first dose of ions, in some embodiments, comprises helium ions, neon ions or argon ions.

In some embodiments of methods described herein, the first dose of ions sufficient to provide a first aperture of predetermined diameter is selected with reference to data derived from one or more reference membranes comprising structures formed by exposure to quantified doses of ions of an ion beam. In some embodiments, the one or more structures formed by exposure to quantified doses of ions of an ion beam comprise apertures in the reference membranes. In some embodiments, characterization of structures of a reference membrane is administered by one or more microscopy techniques. In some embodiments, for example, aperture structures formed in a reference membrane by exposure to quantified doses of ions are characterized by TEM.

In some embodiments, a reference membrane comprises the same material or a substantially similar material as the solid state membrane exposed to the first dose of ions. Moreover, in some embodiments, a reference membrane has one or more dimensions identical or similar to the solid state membrane exposed to the first dose of ions. Additionally, in some embodiments, the ion beam providing quantified doses of ions to a reference membrane has one or more parameters in common with the ion beam impinging on the surface of the solid state membrane at the first location. In some embodiments, for example, an ion beam providing quantified doses of ions to a reference membrane has the same or substantially the same focal point diameter as the ion beam impinging on the surface of the solid state membrane at the first location. Additionally, in some embodiments, the ion beam providing quantified ion doses to a reference membrane employs the same ion as the ion beam impinging on the surface of the solid state membrane at the first location.

Figure 1:
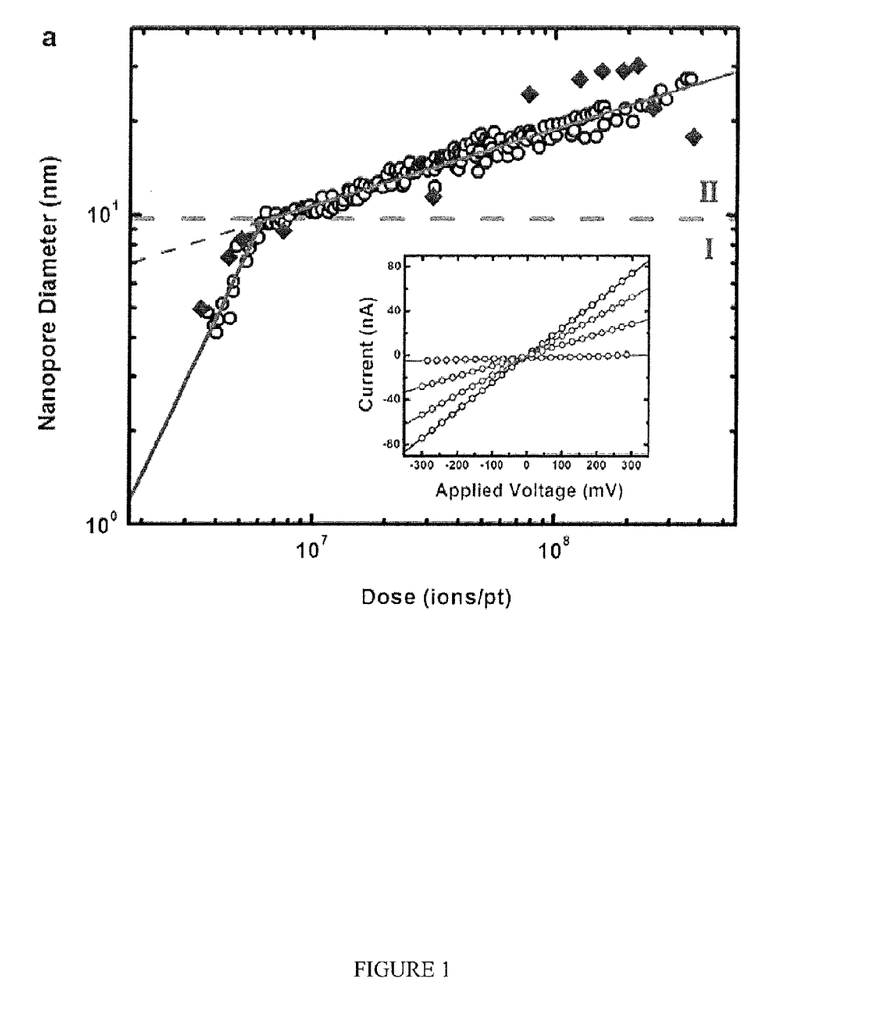
FIG. 1 illustrates ion dose reference data derived from reference membranes comprising structures formed by exposure to quantified doses of helium ($He^+$) ions of an ion beam according to one embodiment described herein.

FIG. 1 illustrates ion dose reference data derived from reference membranes comprising apertures formed by exposure to quantified doses of helium ($He^+$) ions of an ion beam according to one embodiment described herein. As illustrated in FIG. 1, a linear relationship is established between total ion dose and resultant nanoaperture size. Specifically, FIG. 1 illustrates two distinct linear regimes. The first regime is associated with a rapid increase in aperture diameter below 10 nm with increasing $He^+$ dose. The second regime demonstrates a slower increase in aperture diameter greater than 10 nm with increasing $He^+$ dose.

Figure 2:
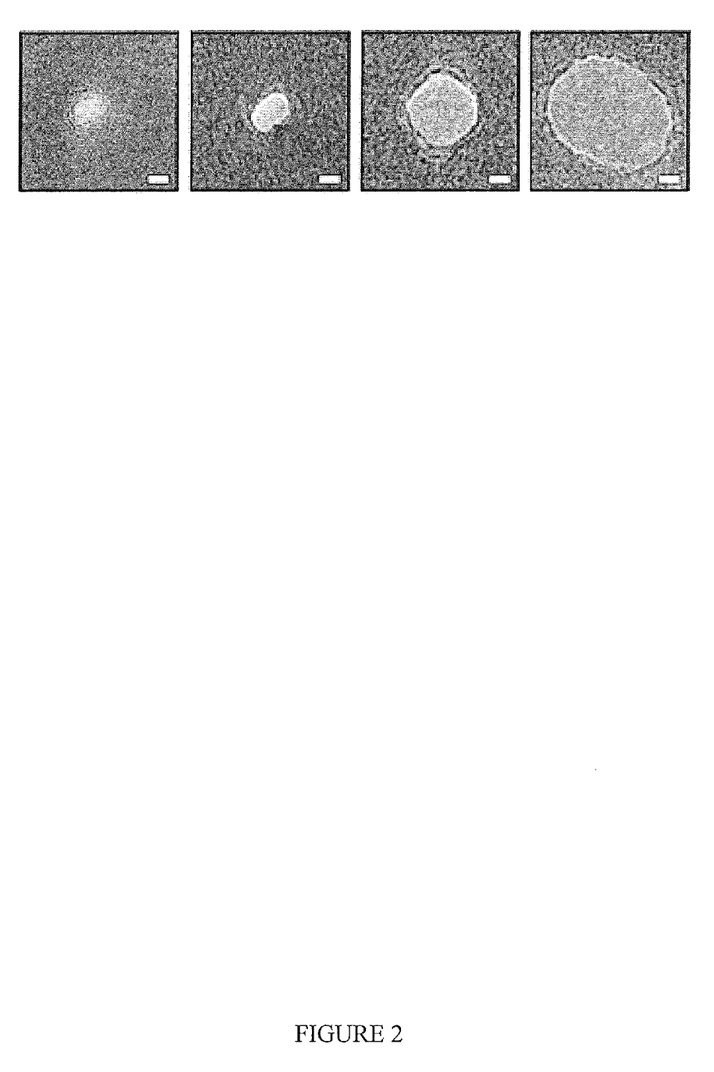
FIG. 2 illustrates transmission electron micrographs of nanoscale apertures formed in solid state membranes according to some embodiments described herein.

FIG. 2 illustrates transmission electron micrographs of nanoscale apertures formed in silicon nitride membranes using a single-step method according to some embodiments described herein. A scanning helium ion microscope (Carl Zeiss Orion Plus HIM) operating at an accelerating voltage of 30-35 kV and a 5 pA beam current and having a probe size of about 5 nm was used to fabricate the nanoscale apertures of FIG. 2. The sizes of the nanoscale apertures from left to right were 3.7 nm, 6.8 nm, 14.6 nm and 25.8 nm.

In some embodiments, a method described herein further comprises selecting an additional dose of ions sufficient to provide an additional aperture of predetermined diameter through the membrane and exposing a surface of the membrane at an additional location to the additional dose of ions in an ion beam. Exposure of the membrane surface to the ion beam removes material from the membrane at the additional location to provide the additional aperture having the predetermined diameter or substantially the predetermined diameter.

In some embodiments, a plurality of additional doses of ions is selected, and surfaces of the membrane are exposed to the additional ion doses in ion beams at additional locations to remove material from the membrane thereby providing additional apertures having the predetermined diameter or substantially the predetermined diameter. The apertures, in some embodiments, are arranged in an array format such as a one-dimensional array or a two-dimensional array. Moreover, in some embodiments, one or more additional apertures in a solid state membrane are fabricated without removing the membrane from the chamber or otherwise further processing the membrane between ion beam exposures.

Figure 3:
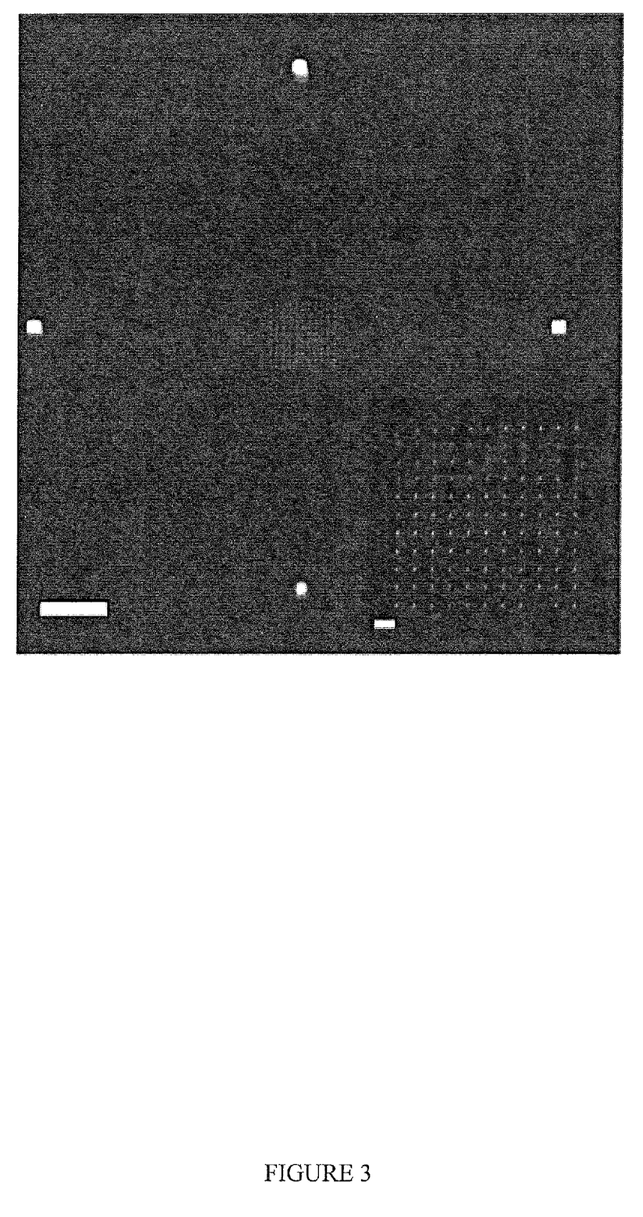
FIG. 3 illustrates an array of nanoscale apertures formed in a solid state membrane according to one embodiment described herein.

FIG. 3 illustrates a transmission mode HIM (Carl Zeiss Orion Plus) image of an 11×11 array of 5 nm nanopores (write time approximately 1 minute) fabricated in a SiN membrane in accordance with a method described herein. The array is surrounded by four patterns of about 100 nm each.

In some embodiments, the ion beam delivering an additional dose of ions has a focal point of diameter less than or equal to about 1 nm. In some embodiments, the ion beam delivering an additional dose of ions is provided by the same apparatus providing the first dose of ions. Additionally, in some embodiments, the ionic species employed in forming the first aperture is also employed in forming the one or more additional apertures. In some embodiments, an ionic species different from that employed to form the first aperture is used in the formation of an additional aperture.

In some embodiments, an additional aperture can have any of the properties recited herein for the first aperture, including aperture diameter. Moreover, in some embodiments, an additional aperture can be formed on a timescale consistent with that recited herein for the first aperture.

An additional dose of ions forming an additional aperture, in some embodiments, is determined by reference to data derived from a reference membrane comprising one or more structures formed by exposure to quantified doses of ions of an ion beam. As described herein, in some embodiments, the reference membrane comprises the same material or a substantially similar material as the solid-state membrane exposed to the additional dose of ions. Moreover, in some embodiments, a reference membrane has one or more dimensions identical to or similar to the solid state membrane exposed to the additional dose of ions.

In some embodiments, an ion beam providing quantified doses of ions to a reference membrane has one or more parameters in common with the ion beam impinging on the surface of the solid state membrane at the additional location. In some embodiments, for example, an ion beam providing quantified doses of ions to a reference membrane has the same or substantially the same focal point diameter as the ion beam impinging on the surface of the solid state membrane at the additional location. In some embodiments, an ion beam providing quantified doses of ions to a reference membrane employs the same ion as the ion beam impinging on the surface of the solid state membrane at the additional location.

In some embodiments, a method of forming an aperture further comprises thinning the solid-state membrane in an area proximate the first aperture. In some embodiments, thinning the membrane comprises exposing an area proximate the first aperture to an ion beam. The ion beam for thinning, in some embodiments, employs the same ionic species as the ion beam for formation of the first aperture. In some embodiments, the ion beam moves in a predetermined pattern to thin the membrane. Additionally, in some embodiments, a dose of ions sufficient to thin the membrane is determined by reference to data derived from one or more reference membranes comprising one or more structures formed by exposure to quantified dose(s) of ions of an ion beam. In some embodiments, thinning of a membrane is administered prior to aperture formation. In some embodiments, thinning of a membrane is administered subsequent to aperture formation. In some embodiments, for example, a region of the membrane is thinned by exposure to an ion beam, and one or more apertures are formed in the thinned region of the membrane.

In some embodiments, thinning of a solid state membrane is administered while the membrane is in the aperture formation chamber. In one embodiment, for example, a membrane is placed in the aperture formation chamber and thinned with an ion beam in an area proximate to where the aperture is to be formed. After completion of the thinning, aperture formation can begin without the need to further process the membrane outside to the chamber prior to aperture formation. In some embodiments, for example, thinning of the membrane is conducted without masking the membrane with a resist and/or exposure to electron beam or chemical etching techniques.

This is in sharp contrast to prior techniques where a membrane is thinned by electron beam lithography, chemical etch or combinations thereof prior to placement in a chamber for exposure to an ion source. In some embodiments, an ion beam used to thin the membrane is the same ion beam used in aperture formation or employs the same ionic species used in aperture formation. In some embodiments, the apparatus used to provide the ion beam during membrane thinning is the same apparatus used to provide the ion beam for aperture formation.

Figure 6:
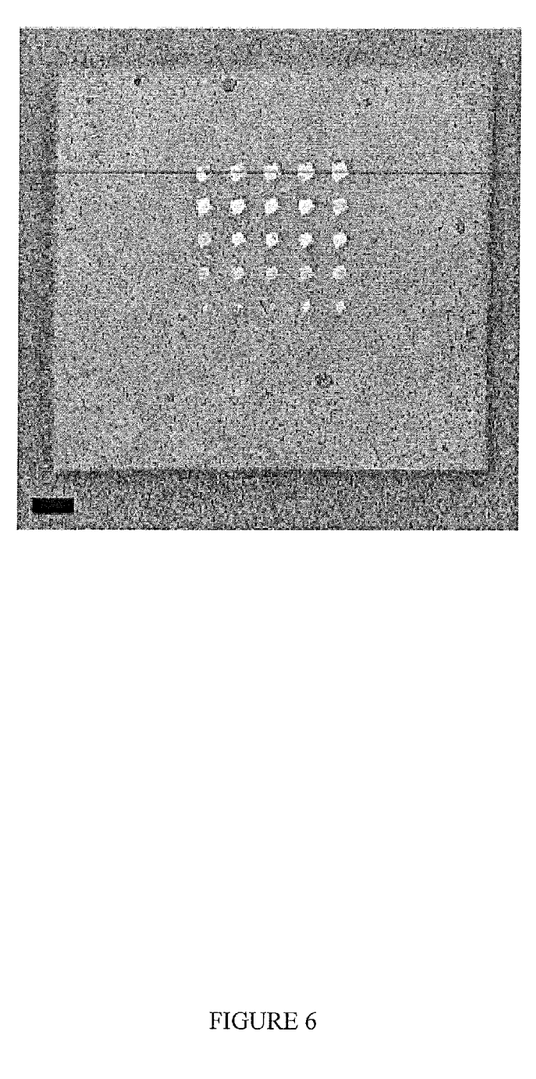
FIG. 6 illustrates a membrane comprising an array of various sized nanoscale apertures formed through a thinned region of the membrane according to one embodiment described herein.

In some embodiments, a solid state membrane can be thinned to any desired thickness. In some embodiments, a solid state membrane is thinned to a thickness of less than 10 nm or less than 5 nm. FIG. 6 illustrates a membrane comprising an array of various sized nanoscale apertures formed through a thinned region of the membrane according to one embodiment described herein. The thinned region (light square) of the membrane of FIG. 6 has a thickness of about 5 nm.

In some embodiments of methods described herein, a plurality of solid state membranes is provided in the chamber, wherein the membranes are exposed to a first dose of ions providing first apertures of predetermined diameter through the membranes as described herein. Moreover, in some embodiments, the membranes are exposed to additional doses of ions at a plurality of additional locations providing additional apertures of predetermined diameter in the membranes as described herein. The ability to co-process a plurality of membranes in a single aperture formation chamber step marks a fundamental departure from prior nanopore fabrication techniques limited to processing only one solid state membrane at a time per aperture formation chamber.

In some embodiments described herein, a method of forming an aperture further comprises exposing the first aperture and/or additional aperture to an unfocused ion beam. Exposure of the first and/or additional aperture to an unfocused ion beam, in some embodiments, reduces the diameter of the aperture. In some embodiments, for example, the diameter of the first aperture is reduced by material transported to the aperture in response to exposure by the defocused ion beam.

In another aspect, a method of nanopore formation described herein comprises providing at least one solid state membrane in a chamber, exposing a surface of the membrane at a first location to a first dose of ions in a focused ion beam sufficient to provide a first aperture of first diameter through the membrane, wherein the first dose of ions falls in a first linear region of a plot of aperture diameter versus ion dose having a slope [(aperture diameter)/(ion dose)] greater than a second linear region of the plot.

FIG. 1 illustrates a plot of aperture diameter versus ion dose comprising a first linear region (I) having a slope greater than the second linear region (II) according to one embodiment described herein. In the embodiment of FIG. 1, the first region (I) is associated with rapid increase in aperture diameter below 10 nm with increasing $He^+$ dose. The second region (II) demonstrates a slower increase in aperture diameter greater than 10 nm with increasing $He^+$ dose. In demonstrating different slopes, the first and second regions can evidence divergent aperture formation mechanisms and divergent aperture geometries and/or structure. As a result, ion dose can be chosen within the first region or the second region according to the desired nanopore geometry and/or structure. An aperture formed according to the present method can have any property recited herein for an aperture, including any value of diameter recited herein. Similarly, a membrane of the present method can have any membrane property recited herein, including membrane composition and/or construction.

In some embodiments, a plot of aperture diameter versus ion dose is produced empirically/experimentally or theoretically. In some embodiments, for example, a plot of aperture diameter versus ion dose can be derived from one or more reference membranes comprising one or more apertures formed by exposure to quantified doses of ions in an ion beam. Alternatively, a plot of aperture diameter versus ion dose, in some embodiments, is theoretically derived according to one or models and/or calculations using parameters including membrane composition, ion identity and/or accelerating voltages.

In some embodiments, the method further comprises exposing a surface of the membrane at a second location to a second dose of ions in a focused ion beam sufficient to provide a second aperture of second diameter through the membrane, wherein the second dose of ions falls in the first linear region or the second linear region of the plot of aperture diameter versus ion dose. In some embodiments, the membrane is exposed to the second dose of ions prior to exposure to the first dose of ions. In some embodiments, the focused ion beam providing the first and/or second doses of ions, according to the present method, has a focal point of diameter less than or equal to 1 nm. Moreover, in some embodiments, the same ionic species is used in the first and second doses.

Further, in some embodiments, the membrane is thinned in an area proximate the first aperture and/or second aperture. In some embodiments, the membrane is thinned while in the aperture formation chamber as described herein.

In another aspect, a method described herein comprises providing at least one solid state membrane in an aperture formation chamber, selecting a first dose of ions sufficient to provide a first aperture through the membrane and exposing a surface of the membrane at a first location to the first dose of ions in an ion beam to provide the first aperture, wherein the membrane is thinned in the formation chamber in an area proximate the first aperture in a step prior or subsequent to formation of the first aperture.

In some embodiments, thinning the membrane comprises exposing an area proximate the first aperture to an ion beam. The ion beam for thinning, in some embodiments, employs the same ionic species as the ion beam for formation of the first aperture. In some embodiments, the ion beam for thinning employs a different ionic species from that used in aperture formation. In some embodiments, the ion beam moves in a predetermined pattern to thin the membrane. Ion thinning of the membrane, in some embodiments, is conducted without e-beam exposure, masking and/or lithographic developing procedures, including chemical etching.

In some embodiments, the method further comprises selecting an additional dose of ions sufficient to provide an additional aperture through the membrane and exposing a surface of the membrane at an additional location to the addition dose of ions in an ion beam to provide the additional aperture. In some embodiments, the membrane in also thinned in the chamber in an area proximate the additional location. In some embodiments, the membrane is thinned in a step prior or subsequent to formation of the additional aperture. Thinning the membrane, in some embodiments, comprises exposing the membrane to an ion beam. In some embodiments, the ion beam for thinning the membrane employs the same ionic species as the ion beam forming the first and/or additional apertures.

Apertures formed according to the present method can have any property recited herein for an aperture, including any value of diameter recited herein. Similarly, membranes of the present method can have any property recited herein for a membrane, including composition and/or construction.

II. Methods of Particle Analysis

In another aspect, methods of conducting particle analysis are described herein. In some embodiments, a method of conducting particle analysis comprises providing a solid state membrane comprising an aperture and passing a particle through the aperture to determine or more properties of the particle, wherein the aperture is formed by any method provided in Section I hereinabove. Any solid state membrane comprising an aperture fabricated according to a method described herein is contemplated for use in the presently described methods of conducting particle analysis.

In some embodiments, the solid state membrane is placed between electrically isolated ionic solutions, wherein one of the solutions comprises the particle(s). A voltage is applied to pass the particle(s) through the aperture in the membrane. In some embodiments, a particle is a biological particle. Biological particles, in some embodiments, comprise nucleic acids, proteins, DNA, RNA, protein complexes, nucleic acid complexes, nucleic acid-protein complexes, viruses or mixtures thereof. Alternatively, a particle is an inorganic particle such as a metal particle or semiconducting particle, including quantum dots. In some embodiments, a particle is a carbon nanoparticle including single-walled carbon nanotubes, multi-walled carbon nanotubes, fullerenes, graphene or mixtures thereof.

Example 1

Nanoscale Aperture Fabrication and Molecular Analysis Quantification

A. Nanoscale Aperture Formation

Free-standing SiN membranes supported across a window in a silicon chip were purchased commercially (Protochips, Raleigh, N.C.). Each chip was rinsed with acetone and ethanol and dried under nitrogen flow before being mounted on a custom HIM sample holder. The holder of the present example had capacity for eight individual chips, but was limited only by the 50 mm travel of the X-Y sample stage. With the current size of silicon support chips, this would allow up to 100 individual SiN membrane chips to be loaded in the HIM at once. The holder containing the samples was treated with oxygen plasma (150 W) for 5 min and immediately loaded into the HIM (Carl Zeiss Orion Plus) sample exchange chamber, where it was exposed to an additional (integrated) air plasma (10 W) for 3 min to ensure minimal contamination before being loaded into the main chamber. Upon loading the samples, beam conditions were set by adjusting the condenser lens, helium gas flow and aperture.

For nanoscale aperture formation presented herein, the HIM beam current was adjusted to 5 pA through a 10 μm aperture. Directly prior to aperture formation at each sample window, beam focus and stigmation were optimized at a nearby area of the substrate. A brief (~10 s) single spot exposure of the beam resulted in a milled mark on the surface that can be used as a feature to tune these conditions using conventional imaging mode. Once corrected, the beam was blanked and the SiN membrane was moved into the beam path. Here, a computer-controlled exposure of a set time was performed to provide a selected dose of $He^+$ to the SiN membrane, ablating material and forming the nanoscale aperture(s). After exposure, if desired, the resultant milled pattern can then be imaged directly using a transmission stage.

Post-fabrication HIM imaging was avoided, as the ion beam may have effects on the resultant nanopore size and shape.

Instead, nanoscale apertures were analyzed using a TEM (JEOL 2010FFasTEM) set at an accelerating voltage of 120 kV, which was generally unable to modify the SiN. For each nanoscale aperture, the area of the opening was measured and an average diameter assuming a perfectly circular pore was calculated. A narrow distribution of aperture diameters (±3 nm on average) resulting from a given exposure was found, indicating the reproducible nature of nanoscale aperture formation according to methods described herein.

B. Noise Analysis and DNA Translocations

Single nanoscale apertures of varying size were fabricated in separate membranes as provided in Section I above. Each membrane was treated on both sides with an oxygen plasma (100 W) before being immediately loaded into a Perspex flow cell containing two chambers with access to either side of the membrane. An electrolyte solution containing 1 M KCl, 10 mM tris-HCl (pH 8.0) and 1 mM EDTA was introduced into each compartment and electrical contact was made using Ag/AgCl electrodes attached to a patch clamp amplifier (Axon 200B, Axon Instruments) for current measurement.

Figure 4:
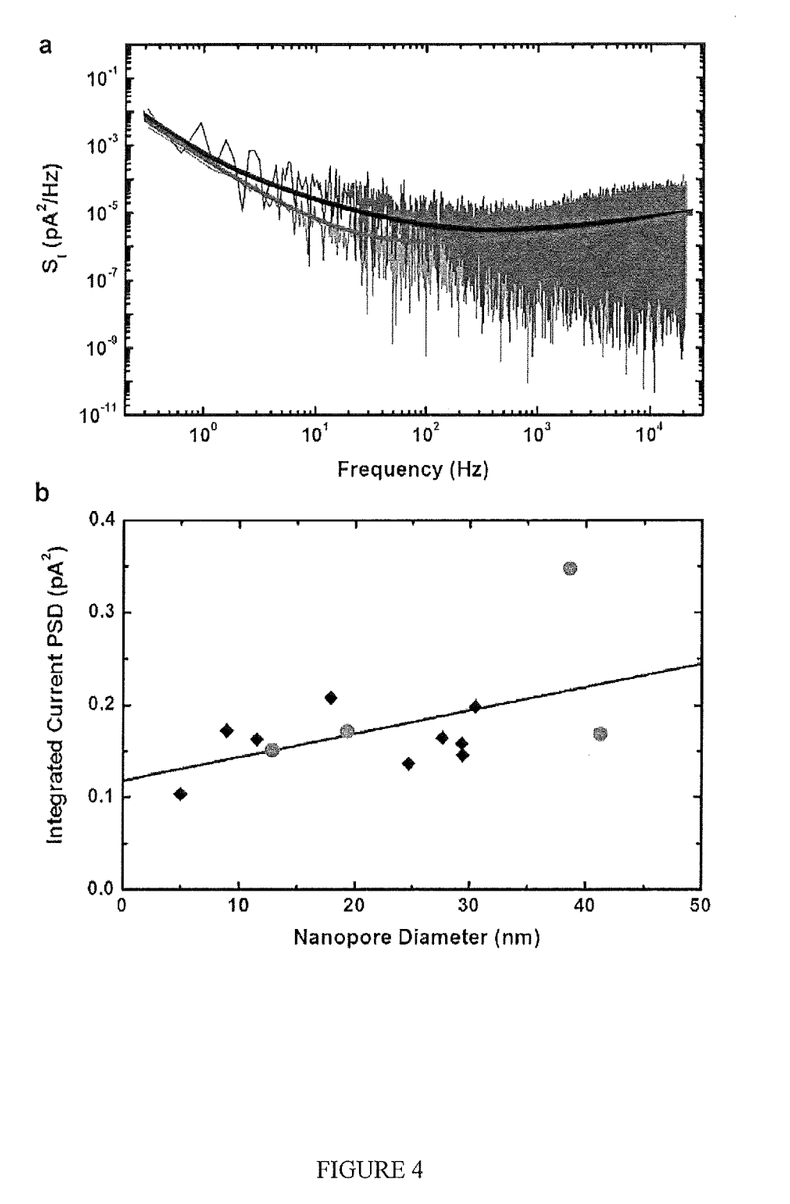
FIG. 4 illustrates an analysis of ionic current noise in a nanopore fabricated according to one embodiment described herein in comparison with a nanopore fabricated according to a prior art TEM technique.

An important aspect of ionic transport measurements is the noise associated with the measurements. The noise levels in TEM nanopores, for example, have been widely studied because signal-to-noise ratio is of central concern to their use in biomolecule detection. We therefore analyzed the current noise in the HIM nanopores of this example and compared them directly with ones formed by TEM in the same type of membrane. For these measurements, 100 mV was applied and current was measured across the nanoscale aperture at a rate of 200 kHz and low pass filtered at 100 kHz before being digitized. FIG. 4(a) displays the current power spectral density (PSD) for both a TEM and an HIM constructed nanopore, each with a diameter of about 12 nm. The crosspectral noise properties between the two are similar, with the TEM nanopore level being slightly lower than that of the HIM nanopore in the intermediate frequency range. By calculating the mathematical integral of the PSD for multiple individual samples made with both methods (HIM and TEM), we found that current noise in fact follows the same general trend in both. From this, it was concluded that the ionic current noise for HIM nanopores fabricated according to some embodiments of methods described herein was comparable to that of TEM nanopores.

Additionally, it was demonstrated that nanopores formed with the HIM milling method according to some embodiments described herein were capable of biomolecule detection by measuring double-strand (ds) DNA translocations. This is the molecule most widely studied with solid-state nanopores and can therefore be considered a standard.

Figure 5:
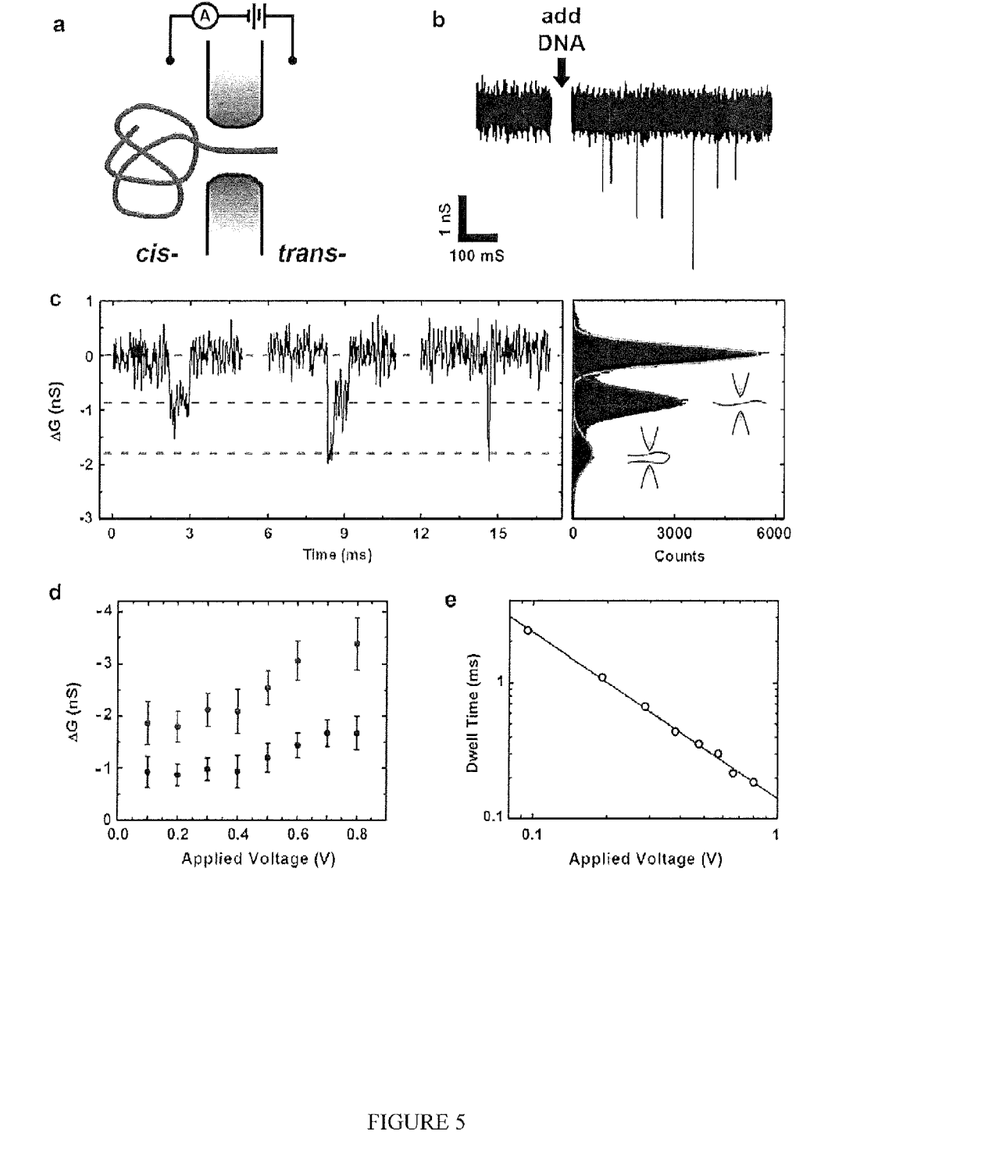
FIG. 5 illustrates various aspects of analysis of DNA transport through a solid state membrane comprising an aperture formed according to one embodiment of a method described herein.

For the experiment, a nanoscale aperture with diameter 24.7 nm was fabricated and cleaned prior to measurement in the same way as described in Section I above. Initial characterization demonstrated linear I-V characteristics with a resistance of 5.6 MΩ and current noise comparable to that discussed above. Next, λ dsDNA (48.5 kb) was loaded into the cis-chamber (FIG. 5(a)) at a concentration of ~300 ng μl$^{-1}$. The subsequent application of a transmembrane voltage resulted in a series of downward spikes in the measured nanopore conductance (FIG. 5(b)), characteristic of dsDNA translocations. Closer analysis (FIG. 5(c), left) revealed the structure within these events that was caused by different folding conformations of the molecule during translocation. Indeed, a histogram of all conductance data points (FIG. 4(b), right) displayed that the measured conductance levels fell into easily separable populations. The HIM nanopore was sufficiently stable to perform this measurement over a large range of applied voltage (100-800 mV), resulting in a total of over 9000 individual recorded events. FIG. 5(d) illustrates the depth ($\Delta G$) of both the unfolded and singly folded conductance levels. An increase was observed in the depths of both types of events over the voltage range, in qualitative agreement with the trend found previously for unfolded translocations. It was also noted that the measured dwell time of events (i.e. the time from the initial conductance drop to its return to the baseline value) exhibited a clear 1/V dependence (FIG. 4(e)), as has been observed previously.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A method of forming an aperture comprising:
providing at least one solid state non-metallic membrane in a chamber;
selecting a first dose of ions sufficient to provide a first aperture of predetermined diameter through the membrane; and
exposing a surface of the membrane at a first location to the first dose of ions through a focused ion beam having a focal point of diameter less than or equal to about 1 nm to remove material from the membrane at the first location providing the first aperture having the predetermined diameter or substantially the predetermined diameter, wherein the first dose of ions is selected with reference to data derived from one or more reference membranes comprising one or more structures formed by exposure to one or more quantified doses of ions of an ion beam.

2. The method of claim 1, wherein the ions are selected from the group consisting of helium, neon and argon.

3. The method of claim 1, wherein the first dose of ions falls in a first linear region of a plot of aperture diameter versus ion dose having a slope [(aperture diameter/ion dose)] greater than a second linear region of the plot.

4. The method of claim 1, wherein the first aperture has a diameter ranging from about 1 nm to about 30 nm.

5. The method of claim 1, wherein the first aperture has a diameter less than 5 nm.

6. The method of claim 1 further comprising thinning the non-metallic membrane in an area proximate the first aperture.

7. The method of claim 6, wherein the non-metallic membrane is thinned while in the chamber.

8. The method of claim 7, wherein the non-metallic membrane in thinned with the same species of ions employed in formation of the first aperture.

9. The method of claim 7, wherein the non-metallic membrane is thinned to a thickness less than 10 nm.

10. The method of claim 1 further comprising selecting an additional dose of ions sufficient to provide an additional aperture of predetermined diameter through the membrane and exposing a surface of the membrane at an additional location to the additional dose of ions in an ion beam.

11. The method of claim 10, wherein the ion beam of additional ions has a focal point less than or equal to about 1 nm.

12. The method of claim 10, wherein the ions of the additional dose are the same species of ion as the first dose.

13. The method of claim 10, wherein the first dose of ions falls in a first linear region of a plot of aperture diameter versus ion dose having a slope [(aperture diameter/ion dose)] greater than a second linear region of the plot, and the additional dose of ions falls in the first linear region or the second linear region of the plot.

14. The method of claim 1, wherein the non-metallic membrane is a ceramic material.

15. A method of forming an aperture comprising:
providing at least one solid state membrane in an aperture formation chamber;
selecting a first dose of ions sufficient to provide a first aperture through the membrane; and
exposing a surface of the membrane at a first location to the first dose of ions in an ion beam to provide the first aperture, wherein the membrane is thinned in the formation chamber in an area proximate the first location.

16. The method of claim 15, wherein the membrane is thinned prior or subsequent to formation of the first aperture.

17. A method of conducting particle analysis comprising:
providing a solid state membrane comprising an aperture; and
passing a particle through the aperture to determine one or more properties of the particle, wherein the aperture is formed according to claim 1.

18. The method of claim 17, wherein the particle is a biological particle.

19. The method of claim 18, wherein the biological particle is selected from the group consisting of nucleic acids, proteins, nucleic acid complexes, protein complexes, nucleic acid-protein complexes and viruses.

20. The method of claim 17 further comprising positioning the solid state membrane between electrically isolated ionic solutions and applying a voltage to the membrane to pass the particle through the aperture.

* * * * *